United States Patent [19]
Marzynski et al.

[11] Patent Number: 5,836,911
[45] Date of Patent: *Nov. 17, 1998

[54] INJECTION DEVICE HAVING POSITIONING MEANS

[75] Inventors: Matthew Marzynski; Paul Mulhauser, both of New York, N.Y.; Dave Schiff, Highland Park, N.J.

[73] Assignee: Medi-Ject Corporation, Minneapolis, Minn.

[*] Notice: This patent issued on a continued prosecution application filed under 37 CFR 1.53(d), and is subject to the twenty year patent term provisions of 35 U.S.C. 154(a)(2).

[21] Appl. No.: 595,140

[22] Filed: Feb. 1, 1996

[51] Int. Cl.$^6$ .................................................. A61M 5/30
[52] U.S. Cl. .......................... 604/72; 604/68; 604/131; 604/135; 604/141; 604/289; 604/293; 222/566; 222/567
[58] Field of Search .................. 604/68, 70–74, 604/19, 36, 48, 39, 116, 69, 117, 131–137, 140, 141, 145–147, 150, 151, 157, 156, 181, 187, 192, 240–243, 232, 218, 257, 261, 263, 264, 268, 275, 289, 293–296, 300–302, 152; 222/108, 402.12, 402.22, 420, 402.21, 402.23, 566–568, 570, 572, 251, 320, 321.1, 321.6, 325–328, 336, 372, 373, 378, 381, 383.1, 383.3, 386, 389, 394, 395

[56] References Cited

U.S. PATENT DOCUMENTS

| | | |
|---|---|---|
| 2,671,447 | 8/1954 | Hein, Jr. . |
| 3,058,466 | 10/1962 | Routsong . |
| 3,934,590 | 1/1976 | Campagna et al. . |
| 4,085,750 | 4/1978 | Bosshold . |
| 4,447,225 | 5/1984 | Taff et al. . |
| 4,518,385 | 5/1985 | Lindmayer et al. . |
| 5,064,413 | 11/1991 | McKinnon et al. . |
| 5,064,420 | 11/1991 | Clarke et al. ............................ 604/301 |
| 5,154,710 | 10/1992 | Williams ................................. 604/301 |
| 5,190,523 | 3/1993 | Lindmayer . |
| 5,207,659 | 5/1993 | Pennaneac'h et al. .................. 604/298 |
| 5,221,027 | 6/1993 | Gibilsco .................................. 222/567 |
| 5,304,151 | 4/1994 | Kuracina . |
| 5,312,335 | 5/1994 | McKinnon et al. ....................... 604/68 |
| 5,312,577 | 5/1994 | Peterson et al. . |
| 5,334,144 | 8/1994 | Alchas et al. . |
| 5,356,380 | 10/1994 | Hoekwater et al. . |

FOREIGN PATENT DOCUMENTS

| | | |
|---|---|---|
| 2028870 | 5/1991 | Canada . |
| 2071115 | 12/1992 | Canada . |
| 0 157 906 | 5/1982 | European Pat. Off. . |

Primary Examiner—Ronald K. Straight, Jr.
Attorney, Agent, or Firm—Pennie & Edmonds LLP

[57] ABSTRACT

A nozzle assembly adapted for an injector, includes a guide for proper application of injections. The guide has first and second wings each extending outwardly and away from the chamber at an angle. These wings are preferably symmetrical and form a V-shape to accommodate appendages such as fingers, toes, or penises. The wings may be curved or straight depending upon the curvature of the substrate to be injected. Also, depending upon the angle layout or length of the wings relative to the chamber and the symmetry of the wings, injections can be set to penetrate at almost any desired angle.

12 Claims, 5 Drawing Sheets

5,836,911

INJECTION DEVICE HAVING POSITIONING MEANS

TECHNICAL FIELD

The present invention relates to an injection device having a guide for positioning the injection device onto a limb, organ or other areas having curved surfaces.

BACKGROUND

Injection devices, particularly devices which do not have visible or exposed needles, are not particularly geared for injecting body appendages, such as arms, fingers, toes, or penises. It is often difficult to align the injector so that it injects toward desired locations on these body parts. For instance, local medication to the penis requires delicate attention, and frequently, medication needs to be injected toward the center of the penis. Unless, the injector is squarely pointing perpendicular to the center of the penis, misalignment can occur, missing the center, or even completely penetrating through the side of it, causing improper or ineffective medication.

One such device is the needleless injector. Needleless injectors administer medication in a fine, high velocity jet, delivering under sufficient pressure to penetrate the skin tissue without requiring a hypodermic needle. These injectors typically have a barrel-like ampule chamber containing a medication. The ampule also has an orifice through which the medication is forced out as a jet by plunger/piston actuated by an energy source, such as a coil spring, gas spring or gas cartridge. Various types of needleless injectors are known in the art, e.g., U.S. Pat. Nos. 5,062,830, 4,790,824 and 4,623,332, etc.

Sometimes it is desirable to angle the injection so that medication goes in at an angle or even off-center. Current needleless injectors and other types of injection devices provide no means for accurately aligning the injection. Thus, there remains a need for a device for providing proper positioning of these types of devices.

SUMMARY

The need for properly positioning injection devices is provided by a nozzle assembly adapted for an injector comprising a chamber for holding a fluid and having a first end, a second end and an orifice for passage of a stream of the fluid, the orifice located at the first end of the chamber, and a guide for guiding the stream of fluid to a curved area of an injection site. The guide preferably comprises first and second wings each extending outwardly and away from the chamber at an angle and forming a V-shape to accommodate the curved area of the injection site therebetween. Advantageously, a plunger is slidingly received in the chamber for expelling fluid out of or drawing fluid into the chamber through the orifice by moving the plunger relative to the chamber. Furthermore, the plunger may be operatively connected to an energy device so that the fluid stream can be expelled under pressure.

Advantageously, the chamber orifice is positioned centrally between the first and second wings and the angle and length of the first wing is substantially the same as the angle of the second wing. Alternatively, the angles or lengths of the first and second wings may be different so that the wings are asymmetric relative to the chamber. Each wing may be curved with a rounded end or be substantially straight depending upon the curvature and configuration of the injection site.

If desired, the guide is formed integrally with the chamber, and the chamber may include a connector adapted for connection to an injector.

BRIEF DESCRIPTION OF THE DRAWINGS

A better understanding of the invention may be obtained from a review of the appended drawing figures, which illustrate preferred embodiments and wherein.

DETAILED DESCRIPTION OF THE DRAWINGS

Figure 2:
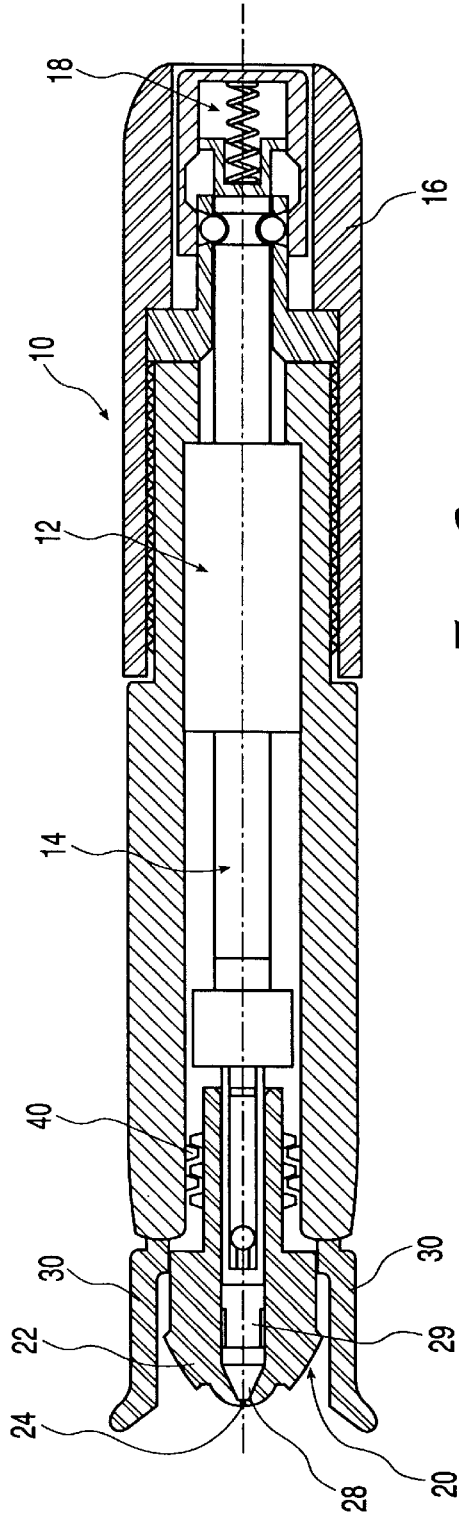
FIG. 2 is a cross-sectional view of an injection device having the nozzle shown in FIG. 1.
Figure 3:
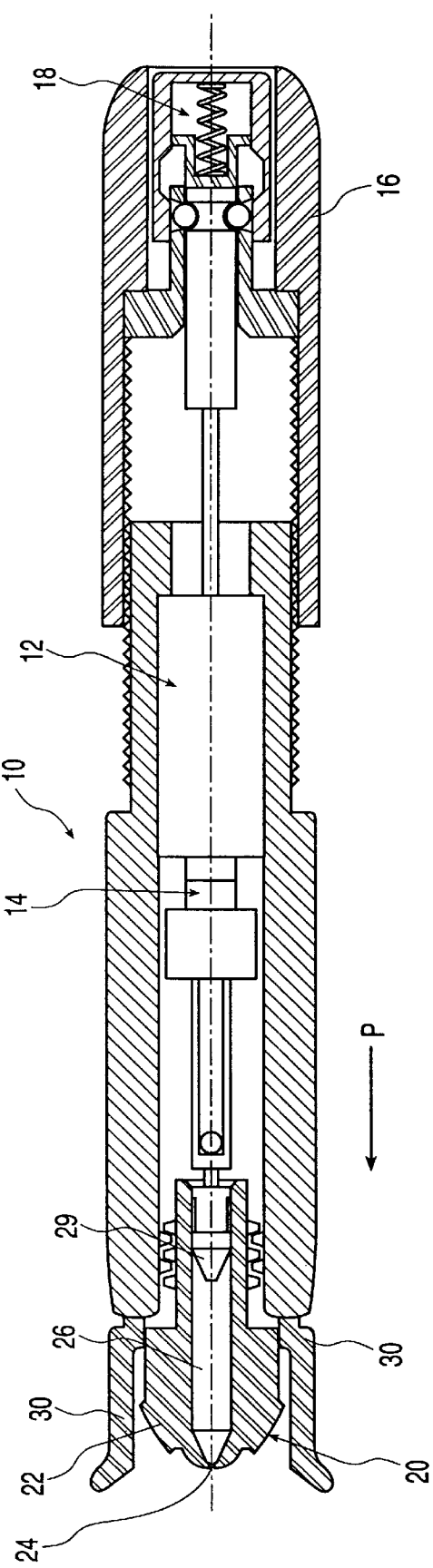
FIG. 3 is a cross-sectional view of the injection device shown in FIG. 2 with the plunger pulled back drawing medication into the nozzle.
Figure 4:
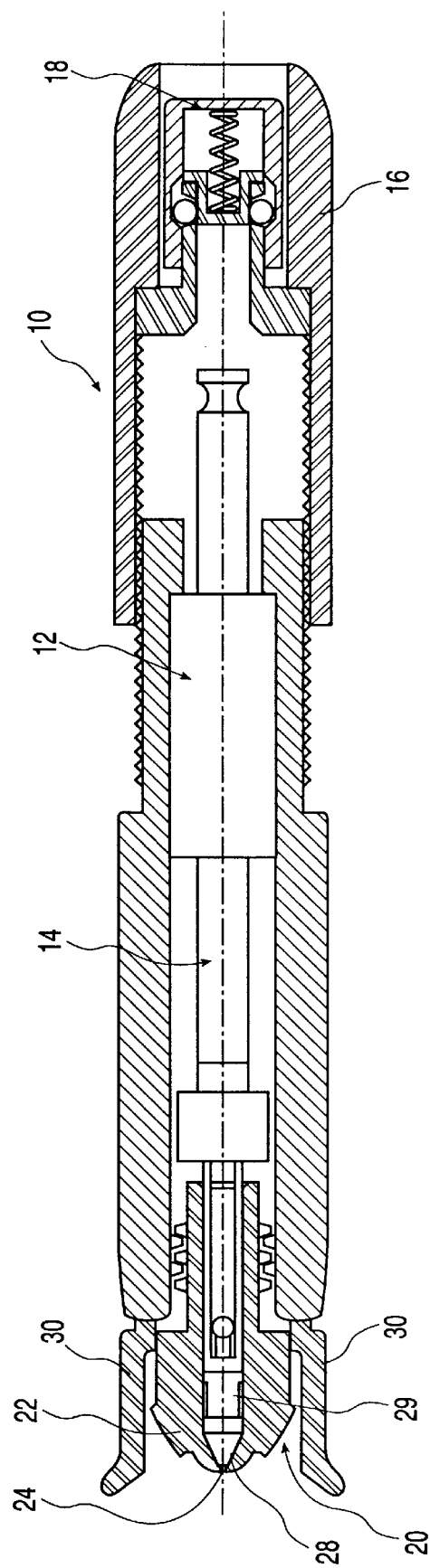
FIG. 4 is a cross-sectional view of the injection device shown in FIG. 3 with the plunger having pushed the medication out of the nozzle.

Referring to the drawings, wherein like reference numbers are used to designate like parts and as shown in FIG. 2, needleless injector 10 comprises an energy device 12, a ram 14, an actuating mechanism 16, a trigger assembly 18, and a nozzle assembly 20. As shown in FIGS. 2, 3 and 4, nozzle assembly 20 is operatively attached to ram 14 which is connected to energy device 12, which can be a gas spring or a coil spring. Actuating mechanism 16 is capable of bringing energy device 12 from a relaxed state to an energized state. The energized state generally describes a situation where the coil spring had been compressed or where the gas contained in the gas spring is further compressed to store energy therein. On the other hand, the relaxed state describes the situation where the energy stored has been expended to drive plunger 14 and the medication out of nozzle 20, i.e., the coil spring or the compressed gas has been expended. Trigger assembly 18 is adapted to retain the energy device 12 in its energized state and comprises a triggering mechanism capable of releasing the energy device so that it may go from the energized state to the relaxed state. Up to this point the needleless injector described has been disclosed in U.S. Pat. No. 5,599,302, and its disclosure is incorporated herein by reference.

Figure 1:
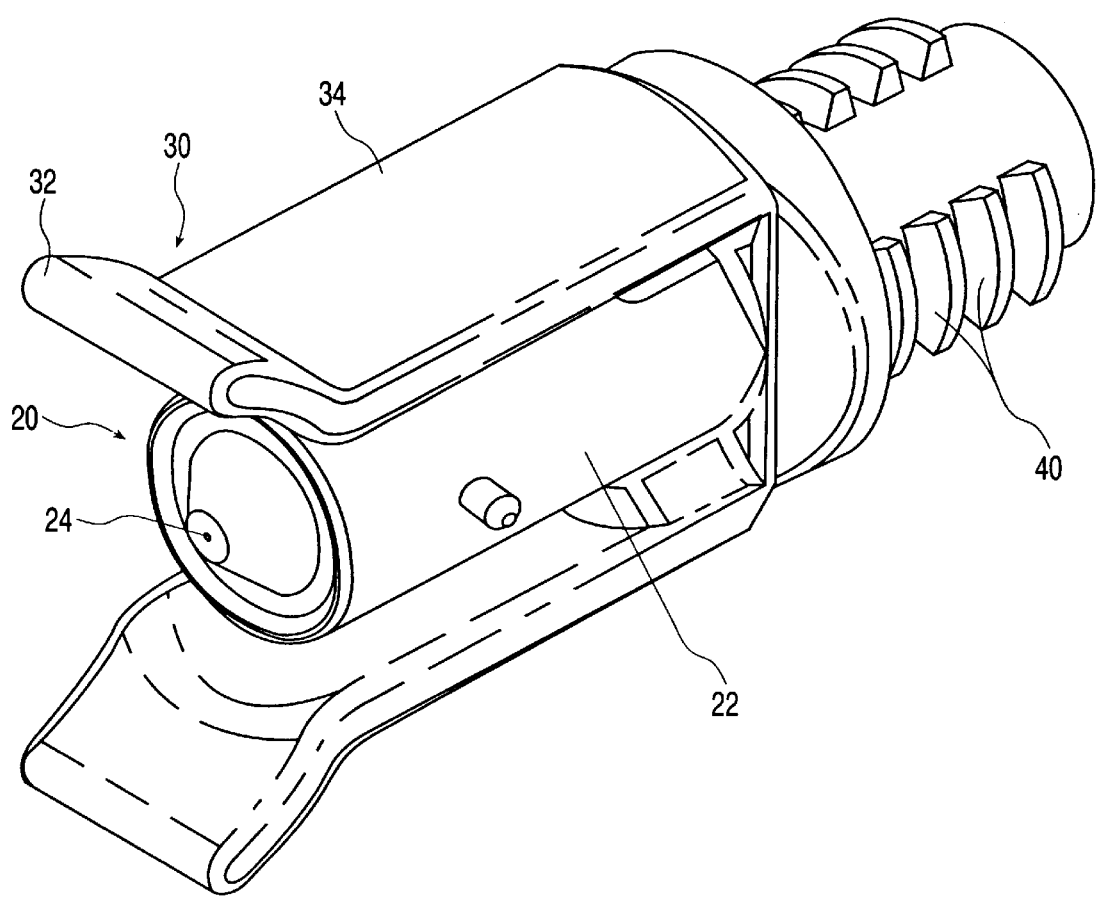
FIG. 1 is a perspective view of a nozzle having guide members according to the present invention.

Nozzle 20 generally comprises main body 22 having an orifice 24 for the medication to be ejected therefrom as shown in FIG. 1. Main body 22 defines an ampule chamber 26 terminating in a right circular cone 28. Plunger 29 having a pressure wall contoured to cone 28 is slideably disposed within main body 22. Additionally, plunger 29 includes sealing means such as an O-ring or the like, formed around the circumference of plunger 29 to provide a seal between plunger 29 and main body 22. Nozzle assembly 20 preferably includes conventional threads or bayonet mounts for removably connecting nozzle assembly 20 to needleless injector 10, as shown in FIGS. 2–4.

Nozzle member 20 has a guide for allowing accurate injection to curved or rounded body parts, such as arms, legs fingers, toes, buttocks, breasts, or penises. The guide comprises a pair of wings 30 each extending outwardly from main body 22 at an angle as shown in FIGS. 1–4. The wings shown are symmetrical and preferably spaced diametrically opposite from each other. Each wing may be curved with a rounded end or be substantially straight depending upon the curvature and configuration of the injection site. These wings preferably form a V-shape to accommodate rounded parts of the body, particularly penises.

An advantage of the invention is that it can be made for use with a specific limb or external organ. For example, as shown in FIGS. 2–4, the wings 30 extend beyond the orifice 24. As depicted, the wings are adapted to partially wrap around a curved injection site such that the orifice would automatically be centered and squared against the site. If this same nozzle assembly were to be used to inject in the thigh or buttock areas, the wings would prevent the orifice from coming into contact with the skin and thereby making injection difficult or if not impossible. Thus, the wings must be designed to accommodate the curved shape of the injection site, and this can be easily determined by one of ordinary skill in the art who has knowledge of the curvature, size and shape of the injection site.

Figure 5:
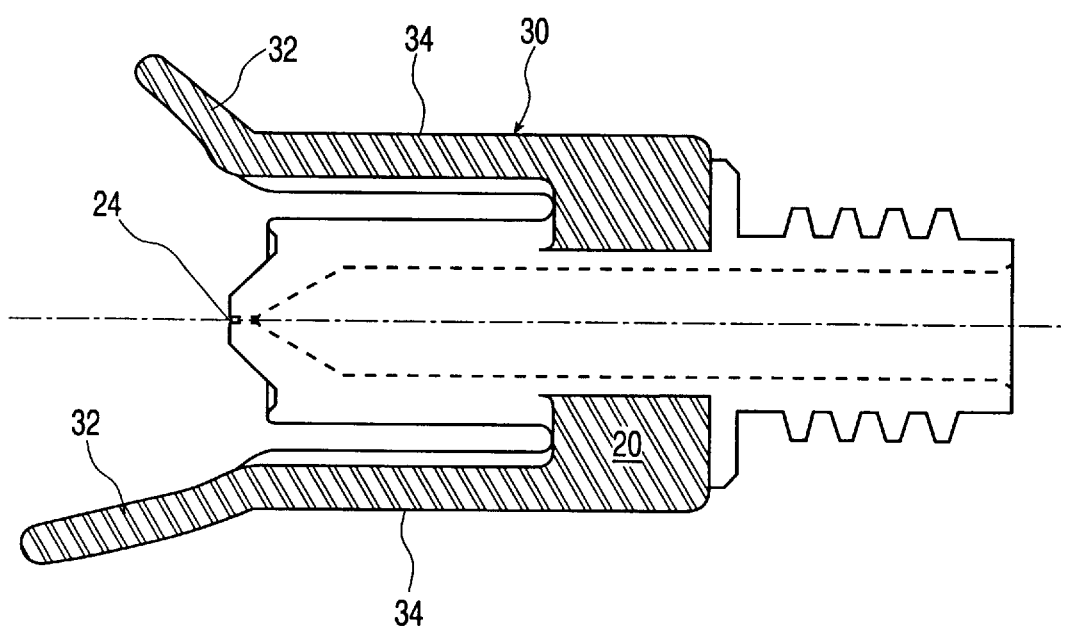
FIG. 5 is a cross-sectional view of another nozzle according to the present invention.

The wings depicted are symmetrical, but can be asymmetrical if desired such that when the guide is properly set on a penis, for example, the injector lies at a non-orthogonal angle relative to the surface of the penis for the purpose of injecting away from the center or at a controlled angle. As shown in FIG. 5, wings 30 are positioned asymmetrical to main body 22, such that an injection out of nozzle 20 through orifice 24 would not reach the center of the limb or organ, but would enter at a non-orthogonal angle relative to the surface thereof.

Although the nozzle assembly 20 can be connected to the injector using any known structures for attaching and detaching the nozzle to/from the device, the present invention preferably contemplates a bayonet-mount, which has diametrically opposed ridges 40. These ridges 40 are first aligned in an opening having a similar cross-sectional configuration provided in an injector so that the ridges can be inserted. Thereafter, the nozzle member 20 is rotated relative to the injector body by a predetermined degree to prevent the nozzle body from detaching in the axial direction. The bayonet-mount enables a quick attachment and detachment of the nozzle assembly. In this regard, the ridges work in conjunction with position settings in the injector to provide several different positions, i.e., set apart 90° or less. This enables the wings to be aligned at various positions relative to the injector body.

Referring to FIGS. 2–4, in operation the nozzle assembly is attached to needleless injector 10 by hooking bayonet mount 40 into a corresponding bayonet mount disposed inside injector 10 at its distal end. As used in this application, the term distal shall designate an end or direction toward the nozzle 20, and the term proximal shall designate an end or direction toward triggered assembly 18. The distal end of plunger 29 and the proximal end portion of the ram 14 can be connected together by any conventional connection that holds these elements together but enables easy separation, such as a ball and slot configuration as depicted. The plunger is fully pushed into ampule chamber 26, in the distal direction to purge air. As the plunger is pulled in the proximal direction, a partial vacuum is established inside the chamber and draws medication in through orifice 24.

If the nozzle assembly comes with a prefilled medication chamber then the plunger is simply connected directly to the ram at the position shown in FIG. 3. Thereupon the activating mechanism 16 brings the energy source 12 to the energized state. Upon energization of the energy source, the trigger assembly 18 is activated to release the energy stored in the energy source, causing the ram to impart a relatively large force P to the plunger, as shown in FIG. 3. This forces the plunger to move distally and ejects medication out of the chamber, as shown in FIG. 4. At this point, the nozzle assembly can be rotated and removed.

FIG. 5 illustrates the embodiment where the wings are at different angles and have different lengths for allowing the orifice to be positioned at a non-perpendicular angle to the body part to be injected. One of ordinary skill in the art can calculate or determine by routine experimentation the appropriate sizes and angles to use to achieve the desired orifice position. Typically, the orifice is aligned at an injection angle of between ±45° from the perpendicular.

Figure 6:
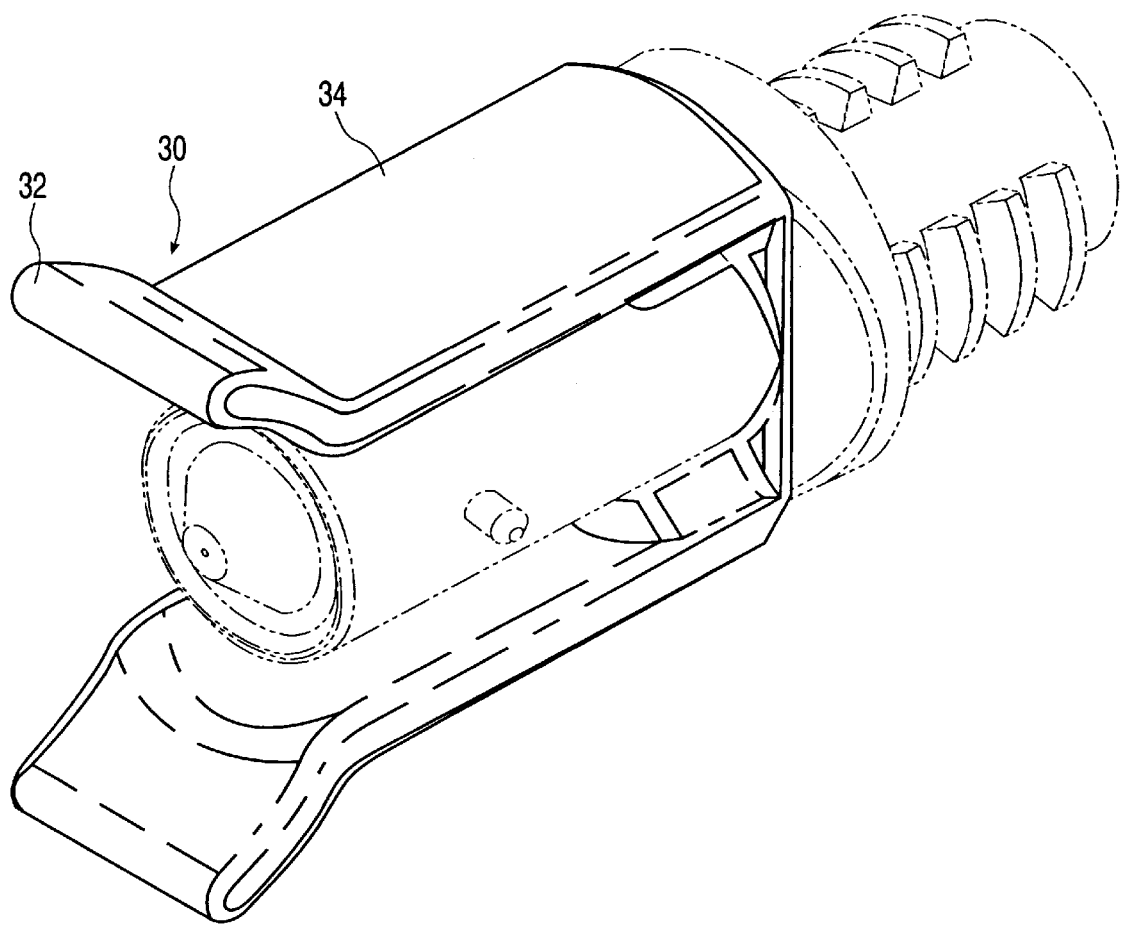
FIG. 6 is a perspective view of a nozzle having guide members according to the present invention in which the guide members are made separately from and removably associated with the chamber.

As shown in FIGS. 1–5, wings 30 comprise straight portions 34 and angled portions 32. Angled portions and straight portions may be manufactured integral with nozzle 20 as shown. However, as shown in FIG. 6 they can be made separately and adapted to slip onto wingless nozzles, such that the wings according to the present invention can be used with existing wingless nozzles. As shown, straight portions have generally cylindrical surfaces to match the contour of nozzle 20. Angled portions 32, however, have relatively flat contour so that angled portions 32 may easily fit around arms, legs or penises.

It should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention accordingly is to be defined as set forth in the appended claims.

What is claimed is:

1. A nozzle assembly adapted for an injector comprising:

a chamber for holding a fluid and having a first end, a second end and an orifice for passage of a stream of the fluid, the orifice located at the first end of the chamber;

a guide for guiding the stream of fluid to a curved area of an injection site, said guide comprising first and second wings, each having a face and extending outwardly and away from the chamber at an angle, said first and second wings together forming a V-shape to accommodate the curved area of the injection site therebetween with the orifice directly contacting the injection site and with the face of each first and second wing at least partially contacting the curved area so as to align the chamber with the curved area for passing the stream of fluid directly into the injection site at a predetermined angle thereto; and a plunger slidingly received in said chamber for expelling fluid out of the chamber through the orifice at a velocity sufficient to penetrate skin tissue by moving the plunger relative to the chamber.

2. The nozzle assembly according to claim 1, wherein the first wing is longer than the second wing.

3. The nozzle assembly according to claim 2, wherein the angles of the first and second wings are different so that the wings are asymmetric relative to the chamber.

4. The nozzle assembly according to claim 1, wherein the plunger is operatively associated with an energy device so that the fluid stream can be expelled at said velocity.

5. The nozzle assembly according to claim 1, wherein the chamber has a connector adapted for connection to an injector.

6. The nozzle assembly according to claim 1, wherein the angle of the first wing is substantially the same as the angle of the second wing.

7. The nozzle assembly according to claim 1, wherein the angles of the first and second wings are different so that the wings are asymmetric relative to the chamber.

8. The nozzle assembly according to claim 1, wherein the guide is formed integrally with the chamber.

9. The nozzle assembly according to claim 1 wherein the chamber orifice is positioned centrally between the first and second wings.

10. The nozzle assembly according to claim 1, wherein each wing is curved and has a rounded end.

11. The nozzle assembly according to claim 1, wherein each wing is substantially straight.

12. The nozzle assembly according to claim 1, wherein the guide is formed separately from and removably associated with the chamber.

* * * * *